(12) United States Patent
Bear et al.

(10) Patent No.: US 9,492,170 B2
(45) Date of Patent: Nov. 15, 2016

(54) DEVICE FOR APPLYING ADJUNCT IN ENDOSCOPIC PROCEDURE

(75) Inventors: Brian W. Bear, Cincinnati, OH (US); Thu Anh Le, Bridgewater, NJ (US); Thomas W. Lytle, IV, Cincinnati, OH (US); Mark D. Overmyer, Cincinnati, OH (US); Michael Setser, Burlington, KY (US); Bret W. Smith, Kings Mills, OH (US); Joseph Zavatsky, Flemington, NJ (US); Kreena Modi, Akron, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 894 days.

(21) Appl. No.: 13/206,752

(22) Filed: Aug. 10, 2011

(65) Prior Publication Data

US 2013/0037596 A1  Feb. 14, 2013

(51) Int. Cl.
*A61B 17/04* (2006.01)
*A61B 17/10* (2006.01)
*A61B 17/072* (2006.01)
*A61B 17/00* (2006.01)
*A61B 17/29* (2006.01)

(52) U.S. Cl.
CPC .... *A61B 17/07207* (2013.01); *A61B 17/07292* (2013.01); *A61B 2017/00495* (2013.01); *A61B 2017/00893* (2013.01); *A61B 2017/07271* (2013.01); *A61B 2017/2927* (2013.01)

(58) Field of Classification Search
CPC .................. A61B 17/068; A61B 2017/00004; A61B 17/105
USPC ........................................... 227/175.1–182.1
See application file for complete search history.

(56) References Cited

U.S. PATENT DOCUMENTS 1,306,107 A * 6/1919 Elliott ........................... 206/346
2,303,131 A   11/1942 Morgan
3,313,289 A * 4/1967 Kapral ..................... 604/288.04
(Continued)

FOREIGN PATENT DOCUMENTS

CA  481943  2/1947
CN  101332110 A  12/2008
(Continued)

OTHER PUBLICATIONS

International Search Report dated Jan. 11, 2013 for Application No. PCT/US2012/050232.
Abstract for FR2789885.
Abstract for FR2850281.
Abstract for JP1072740.
Abstract for JP11309151.
Abstract for JP3146773.
Abstract for JP5076586.
International Preliminary Report on Patentability dated Feb. 11, 2014 for Application No. PCT/US2012/050232.
(Continued)

*Primary Examiner* — Robert Long
(74) *Attorney, Agent, or Firm* — Frost Brown Todd LLC

(57) ABSTRACT

A modular end effector delivers a therapeutic agent onto tissue that has been severed and/or stapled. The end effector is removably attached to a device. The device applies force to a piston of the end effector. The force causes a distal movement of a piston along a wall disposed within the end effector. The piston engages with agents stored on opposite sides of the wall, moving the agents distally to a mixture space. The agents are mixed in the mixture space and expelled through a tip. Staples may be embedded in or disposed below a foam block, which is disposed within a staple cartridge. Via an endoscopic stapling device, coated staples are driven through tissue while interacting with another agent on the device or the cartridge. The interaction forms a tissue restoring material that is applied onto the tissue.

15 Claims, 10 Drawing Sheets

(56) References Cited

U.S. PATENT DOCUMENTS

| | | | |
|---|---|---|---|
| 3,364,200 A | 1/1968 | Ashton et al. | |
| 3,496,940 A | 2/1970 | Steinman | |
| 3,526,228 A | 9/1970 | Lyng | |
| 3,981,051 A * | 9/1976 | Brumlik | 24/447 |
| 3,993,072 A * | 11/1976 | Zaffaroni | 424/430 |
| 4,061,405 A * | 12/1977 | Minter | 439/83 |
| 4,129,059 A * | 12/1978 | Van Eck | 411/475 |
| 4,198,734 A * | 4/1980 | Brumlik | 24/449 |
| 4,222,383 A | 9/1980 | Schossow | |
| 4,309,776 A * | 1/1982 | Berguer | 623/1.41 |
| 4,333,565 A * | 6/1982 | Woods | 206/719 |
| 4,382,326 A * | 5/1983 | Rabuse | 29/270 |
| 4,409,057 A * | 10/1983 | Molenda et al. | 156/92 |
| 4,513,746 A | 4/1985 | Aranyi et al. | |
| 4,548,202 A * | 10/1985 | Duncan | 606/220 |
| 4,549,545 A | 10/1985 | Levy | |
| 4,610,250 A | 9/1986 | Green | |
| 4,616,650 A * | 10/1986 | Green | A61B 17/128 606/143 |
| 4,693,720 A | 9/1987 | Scharnberg et al. | |
| 4,711,351 A * | 12/1987 | Zucker et al. | 206/726 |
| 4,766,031 A * | 8/1988 | Kohl | 428/317.9 |
| 4,805,823 A | 2/1989 | Rothfuss | |
| 4,941,751 A | 7/1990 | Muhlbauer | |
| 5,011,493 A | 4/1991 | Belykh et al. | |
| 5,064,057 A | 11/1991 | Iwatsuki et al. | |
| 5,116,357 A * | 5/1992 | Eberbach | 606/213 |
| 5,242,457 A * | 9/1993 | Akopov et al. | 606/144 |
| 5,263,629 A | 11/1993 | Trumbull et al. | |
| 5,282,829 A | 2/1994 | Hermes | |
| 5,297,324 A | 3/1994 | Su | |
| 5,314,471 A * | 5/1994 | Brauker et al. | 623/23.72 |
| 5,327,914 A | 7/1994 | Shlain | |
| 5,350,388 A * | 9/1994 | Epstein | 606/154 |
| 5,366,480 A | 11/1994 | Corriveau et al. | |
| 5,383,904 A | 1/1995 | Totakura et al. | |
| 5,393,594 A | 2/1995 | Koyfman et al. | |
| 5,411,193 A | 5/1995 | Culp | |
| 5,415,334 A | 5/1995 | Williamson, IV et al. | |
| 5,441,193 A * | 8/1995 | Gravener | 227/176.1 |
| 5,443,508 A * | 8/1995 | Giampapa | 623/23.72 |
| 5,465,895 A | 11/1995 | Knodel et al. | |
| 5,466,462 A | 11/1995 | Rosenthal et al. | |
| 5,477,966 A * | 12/1995 | Ogawa | 206/723 |
| 5,496,603 A | 3/1996 | Riedel et al. | |
| 5,503,638 A | 4/1996 | Cooper et al. | |
| 5,519,893 A * | 5/1996 | Silver | 2/321 |
| 5,542,594 A | 8/1996 | McKean et al. | |
| 5,554,148 A * | 9/1996 | Aebischer et al. | 604/890.1 |
| 5,565,210 A | 10/1996 | Rosenthal et al. | |
| 5,597,107 A | 1/1997 | Knodel et al. | |
| 5,607,590 A | 3/1997 | Shimizu | |
| 5,607,686 A | 3/1997 | Totakura et al. | |
| 5,632,432 A | 5/1997 | Schulze et al. | |
| 5,639,851 A | 6/1997 | Bezwada et al. | |
| 5,641,566 A | 6/1997 | Kranzler et al. | |
| 5,644,002 A | 7/1997 | Cooper et al. | |
| 5,655,698 A * | 8/1997 | Yoon | 227/176.1 |
| 5,662,260 A * | 9/1997 | Yoon | 227/176.1 |
| 5,673,840 A | 10/1997 | Schulze et al. | |
| 5,686,090 A * | 11/1997 | Schilder et al. | 424/423 |
| 5,690,675 A | 11/1997 | Sawyer et al. | |
| 5,704,534 A | 1/1998 | Huitema et al. | |
| 5,711,958 A | 1/1998 | Cohn et al. | |
| 5,733,308 A | 3/1998 | Daugherty et al. | |
| 5,749,968 A | 5/1998 | Melanson et al. | |
| 5,752,965 A | 5/1998 | Francis et al. | |
| 5,755,778 A | 5/1998 | Kleshinski | |
| 5,766,188 A | 6/1998 | Igaki | |
| 5,769,892 A | 6/1998 | Kingwell | |
| 5,810,855 A | 9/1998 | Rayburn et al. | |
| 5,814,055 A | 9/1998 | Knodel et al. | |
| 5,814,057 A | 9/1998 | Oi et al. | |
| 5,843,096 A | 12/1998 | Igaki et al. | |
| 5,902,312 A | 5/1999 | Frater et al. | |
| 5,908,427 A * | 6/1999 | McKean | A61B 17/07207 606/139 |
| 5,997,895 A | 12/1999 | Narotam et al. | |
| 6,019,791 A | 2/2000 | Wood | |
| 6,031,148 A | 2/2000 | Hayes et al. | |
| 6,099,551 A | 8/2000 | Gabbay | |
| 6,174,333 B1 | 1/2001 | Kadiyala et al. | |
| 6,200,330 B1 * | 3/2001 | Benderev et al. | 606/232 |
| 6,203,564 B1 | 3/2001 | Hutton et al. | |
| 6,245,081 B1 | 6/2001 | Bowman et al. | |
| 6,273,897 B1 | 8/2001 | Dalessandro et al. | |
| 6,277,397 B1 | 8/2001 | Shimizu | |
| 6,312,474 B1 | 11/2001 | Francis et al. | |
| 6,325,810 B1 | 12/2001 | Hamilton et al. | |
| 6,355,699 B1 | 3/2002 | Vyakarnam et al. | |
| 6,383,201 B1 * | 5/2002 | Dong | 606/151 |
| 6,413,274 B1 * | 7/2002 | Pedros | 623/2.11 |
| 6,478,776 B1 * | 11/2002 | Rosenman et al. | 604/164.01 |
| 6,488,197 B1 | 12/2002 | Whitman | |
| 6,495,127 B1 | 12/2002 | Wallace et al. | |
| 6,511,748 B1 | 1/2003 | Barrows | |
| 6,592,597 B2 | 7/2003 | Grant et al. | |
| 6,599,318 B1 * | 7/2003 | Gabbay | 623/11.11 |
| 6,638,285 B2 | 10/2003 | Gabbay | |
| 6,652,595 B1 * | 11/2003 | Nicolo | 623/23.74 |
| 6,656,193 B2 | 12/2003 | Grant et al. | |
| 6,704,210 B1 | 3/2004 | Myers | |
| 6,814,741 B2 | 11/2004 | Bowman et al. | |
| 6,835,336 B2 | 12/2004 | Watt | |
| 6,921,412 B1 | 7/2005 | Black et al. | |
| 6,926,723 B1 * | 8/2005 | Mulhauser et al. | 606/151 |
| 6,962,594 B1 | 11/2005 | Thevenet | |
| 6,964,363 B2 | 11/2005 | Wales et al. | |
| 6,974,462 B2 * | 12/2005 | Sater | 606/232 |
| 6,978,921 B2 | 12/2005 | Shelton, IV et al. | |
| 6,988,649 B2 | 1/2006 | Shelton, IV et al. | |
| 7,000,818 B2 | 2/2006 | Shelton, IV et al. | |
| 7,048,755 B2 | 5/2006 | Bonutti et al. | |
| 7,084,082 B2 | 8/2006 | Shimizu | |
| 7,111,769 B2 | 9/2006 | Wales et al. | |
| 7,143,923 B2 | 12/2006 | Shelton, IV et al. | |
| 7,147,138 B2 | 12/2006 | Shelton, IV | |
| 7,207,471 B2 | 4/2007 | Heinrich et al. | |
| 7,211,093 B2 | 5/2007 | Sauer et al. | |
| 7,268,205 B2 | 9/2007 | Williams et al. | |
| 7,303,108 B2 | 12/2007 | Shelton, IV | |
| 7,326,213 B2 * | 2/2008 | Benderev et al. | 606/139 |
| 7,335,212 B2 | 2/2008 | Edoga et al. | |
| 7,367,485 B2 | 5/2008 | Shelton, IV et al. | |
| 7,377,928 B2 | 5/2008 | Zubik et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,455,208 B2 | 11/2008 | Wales et al. | |
| 7,510,566 B2 * | 3/2009 | Jacobs et al. | 606/215 |
| 7,517,356 B2 | 4/2009 | Heinrich | |
| 7,607,557 B2 | 10/2009 | Shelton, IV et al. | |
| 7,686,759 B2 * | 3/2010 | Sater | 600/29 |
| 7,708,180 B2 | 5/2010 | Murray et al. | |
| 7,721,930 B2 | 5/2010 | McKenna et al. | |
| 7,738,971 B2 | 6/2010 | Swayze et al. | |
| 7,845,533 B2 | 12/2010 | Marczyk et al. | |
| 7,857,813 B2 * | 12/2010 | Schmitz et al. | 606/79 |
| 7,861,893 B2 | 1/2011 | Voegele et al. | |
| 7,901,397 B2 * | 3/2011 | Santini et al. | 604/890.1 |
| 7,942,890 B2 * | 5/2011 | D'Agostino | D61B 17/072 606/153 |
| 7,950,561 B2 * | 5/2011 | Aranyi | A61B 17/07207 227/175.1 |
| 8,011,555 B2 * | 9/2011 | Tarinelli | A61B 17/07207 227/175.1 |
| 8,028,883 B2 * | 10/2011 | Stopek | A61B 17/072 227/175.1 |
| 8,100,310 B2 * | 1/2012 | Zemlok | 227/178.1 |
| 8,181,840 B2 * | 5/2012 | Milliman | A61B 17/115 227/175.1 |
| 8,211,131 B2 * | 7/2012 | Golden et al. | 606/153 |
| 8,215,310 B2 * | 7/2012 | Browning | 128/834 |

(56) References Cited

U.S. PATENT DOCUMENTS

| | | | |
|---|---|---|---|
| 8,257,356 B2* | 9/2012 | Bleich et al. | 606/79 |
| 8,361,164 B2* | 1/2013 | Hoganson | 623/23.74 |
| 8,388,633 B2* | 3/2013 | Rousseau et al. | 606/151 |
| 8,464,922 B2* | 6/2013 | Marczyk | 227/176.1 |
| 8,485,412 B2* | 7/2013 | Shelton et al. | 227/176.1 |
| 8,499,993 B2* | 8/2013 | Shelton et al. | 227/178.1 |
| 8,500,762 B2* | 8/2013 | Sholev et al. | 606/151 |
| 8,585,721 B2* | 11/2013 | Kirsch | 606/151 |
| 8,657,176 B2* | 2/2014 | Shelton, IV | A61B 17/00491 227/178.1 |
| 2001/0044637 A1* | 11/2001 | Jacobs et al. | 606/221 |
| 2002/0103494 A1* | 8/2002 | Pacey | 606/151 |
| 2002/0165559 A1 | 11/2002 | Grant et al. | |
| 2003/0120284 A1 | 6/2003 | Palacios et al. | |
| 2003/0183671 A1 | 10/2003 | Mooradian et al. | |
| 2004/0073222 A1* | 4/2004 | Koseki | 606/75 |
| 2004/0093024 A1 | 5/2004 | Lousararian et al. | |
| 2004/0167572 A1 | 8/2004 | Roth et al. | |
| 2004/0236419 A1* | 11/2004 | Milo | 623/2.36 |
| 2004/0254608 A1 | 12/2004 | Huitema et al. | |
| 2005/0042250 A1 | 2/2005 | Damien et al. | |
| 2005/0059996 A1 | 3/2005 | Bauman et al. | |
| 2005/0070929 A1 | 3/2005 | Dalessandro et al. | |
| 2005/0075657 A1* | 4/2005 | Bombard et al. | 606/153 |
| 2005/0101834 A1 | 5/2005 | Merade | |
| 2005/0107810 A1 | 5/2005 | Morales et al. | |
| 2005/0145671 A1 | 7/2005 | Viola | |
| 2005/0154403 A1 | 7/2005 | Sauer et al. | |
| 2005/0154406 A1* | 7/2005 | Bombard et al. | 606/153 |
| 2005/0245965 A1 | 11/2005 | Orban, III et al. | |
| 2005/0249772 A1 | 11/2005 | Maliviya et al. | |
| 2005/0251153 A1 | 11/2005 | Sakamoto et al. | |
| 2005/0267325 A1* | 12/2005 | Bouchier et al. | 600/37 |
| 2005/0276959 A1* | 12/2005 | DeMasi | 428/292.1 |
| 2005/0283256 A1 | 12/2005 | Sommerich et al. | |
| 2005/0288767 A1 | 12/2005 | Kujawski et al. | |
| 2006/0004388 A1 | 1/2006 | Whayne et al. | |
| 2006/0004407 A1 | 1/2006 | Hiles et al. | |
| 2006/0047312 A1 | 3/2006 | Olmo et al. | |
| 2006/0089525 A1* | 4/2006 | Mamo et al. | 600/37 |
| 2006/0093655 A1 | 5/2006 | Bar et al. | |
| 2006/0094318 A1 | 5/2006 | Matsuda et al. | |
| 2006/0135992 A1 | 6/2006 | Bettuchi et al. | |
| 2006/0173470 A1 | 8/2006 | Oray et al. | |
| 2006/0212069 A1 | 9/2006 | Shelton, IV | |
| 2006/0229672 A1 | 10/2006 | Forsberg | |
| 2006/0265006 A1 | 11/2006 | White et al. | |
| 2006/0265007 A1 | 11/2006 | White et al. | |
| 2007/0016227 A1 | 1/2007 | de la Torre et al. | |
| 2007/0034667 A1 | 2/2007 | Holsten et al. | |
| 2007/0034669 A1 | 2/2007 | de la Torre et al. | |
| 2007/0049953 A2 | 3/2007 | Shimoji et al. | |
| 2007/0060932 A1 | 3/2007 | Stack et al. | |
| 2007/0066981 A1 | 3/2007 | Meagher | |
| 2007/0112360 A1 | 5/2007 | De Deyne et al. | |
| 2007/0128243 A1 | 6/2007 | Serafica et al. | |
| 2007/0131732 A1 | 6/2007 | Holsten et al. | |
| 2007/0150002 A1 | 6/2007 | Szabo et al. | |
| 2007/0156140 A1 | 7/2007 | Baily | |
| 2007/0190108 A1 | 8/2007 | Datta et al. | |
| 2007/0207180 A1 | 9/2007 | Tanihara et al. | |
| 2007/0213522 A1 | 9/2007 | Harris et al. | |
| 2007/0219571 A1 | 9/2007 | Balbierz et al. | |
| 2007/0225642 A1 | 9/2007 | Houser et al. | |
| 2007/0243227 A1 | 10/2007 | Gertner | |
| 2007/0246505 A1 | 10/2007 | Pace-Floridia et al. | |
| 2007/0286892 A1 | 12/2007 | Herzberg et al. | |
| 2008/0039871 A1 | 2/2008 | Wallace et al. | |
| 2008/0077131 A1 | 3/2008 | Yates | |
| 2008/0078800 A1 | 4/2008 | Hess et al. | |
| 2008/0078801 A1 | 4/2008 | Shelton, IV et al. | |
| 2008/0078802 A1 | 4/2008 | Hess et al. | |
| 2008/0078803 A1 | 4/2008 | Shelton, IV et al. | |
| 2008/0078804 A1 | 4/2008 | Shelton, IV et al. | |
| 2008/0078805 A1 | 4/2008 | Omaits et al. | |
| 2008/0078806 A1 | 4/2008 | Omaits et al. | |
| 2008/0078807 A1 | 4/2008 | Hess et al. | |
| 2008/0081881 A1 | 4/2008 | Swetlin et al. | |
| 2008/0082124 A1 | 4/2008 | Hess et al. | |
| 2008/0082126 A1 | 4/2008 | Murray et al. | |
| 2008/0110959 A1 | 5/2008 | Orban, III et al. | |
| 2008/0114381 A1 | 5/2008 | Voegele et al. | |
| 2008/0114385 A1 | 5/2008 | Byrum et al. | |
| 2008/0114399 A1 | 5/2008 | Bonutti | |
| 2008/0125812 A1 | 5/2008 | Zubik et al. | |
| 2008/0128469 A1 | 6/2008 | Dalessandro et al. | |
| 2008/0140115 A1 | 6/2008 | Stopek | |
| 2008/0167680 A1 | 7/2008 | Voegele et al. | |
| 2008/0200949 A1 | 8/2008 | Hiles et al. | |
| 2008/0314960 A1 | 12/2008 | Marczyk et al. | |
| 2009/0001122 A1* | 1/2009 | Prommersberger et al. | 227/176.1 |
| 2009/0076510 A1 | 3/2009 | Bell et al. | |
| 2009/0118747 A1 | 5/2009 | Bettuchi et al. | |
| 2009/0188964 A1* | 7/2009 | Orlov | 227/175.3 |
| 2009/0206141 A1* | 8/2009 | Huitema et al. | 227/176.1 |
| 2010/0065606 A1* | 3/2010 | Stopek | 227/176.1 |
| 2012/0187179 A1* | 7/2012 | Gleiman | A61B 17/072 227/176.1 |
| 2012/0273547 A1* | 11/2012 | Hodgkinson | A61B 17/07207 227/176.1 |
| 2013/0161374 A1* | 6/2013 | Swayze et al. | 227/176.1 |

FOREIGN PATENT DOCUMENTS

| | | |
|---|---|---|
| EP | 328 401 | 8/1989 |
| EP | 0 667 119 | 8/1995 |
| EP | 0 781 564 | 7/1997 |
| EP | 0 818 470 | 1/1998 |
| EP | 0 909 590 | 4/1999 |
| EP | 1 064 883 | 1/2001 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| EP | 1 994 890 | 11/2008 |
| FR | 2 668 060 | 4/1992 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 97/21394 | 6/1997 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Chinese Office Action dated Sep. 25, 2015 for Application No. 2012800390406, 7 pages.

Japanese Office Action dated Jul. 19, 2016 for Application No. 2014-525161, 4 pages.

* cited by examiner

DEVICE FOR APPLYING ADJUNCT IN ENDOSCOPIC PROCEDURE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,964,363, entitled "Surgical Stapling Instrument having Articulation Joint Support Plates for Supporting a Firing Bar," issued Nov. 15, 2005; U.S. Pat. No. 6,978,921, entitled "Surgical Stapling Instrument Incorporating an E-Beam Firing Mechanism," issued Dec. 27, 2005; U.S. Pat. No. 6,988,649, entitled "Surgical Stapling Instrument Having a Spent Cartridge Lockout," issued Jan. 24, 2006; U.S. Pat. No. 7,000,818, entitled "Surgical Stapling Instrument Having Separate Distinct Closing and Firing Systems," issued Feb. 21, 2006; U.S. Pat. No. 7,111,769, entitled "Surgical Instrument Incorporating an Articulation Mechanism having Rotation about the Longitudinal Axis," issued Sep. 26, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument having Multistroke Firing with Opening Lockout," issued Oct. 14, 2008; U.S. Pat. No. 7,721,930, entitled "Disposable Cartridge with Adhesive for Use with a Stapling Device," issued May 25, 2010; and U.S. Pat. No. 7,455,208, entitled "Surgical Instrument with Articulating Shaft with Rigid Firing Bar Supports," issued Nov. 25, 2008. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
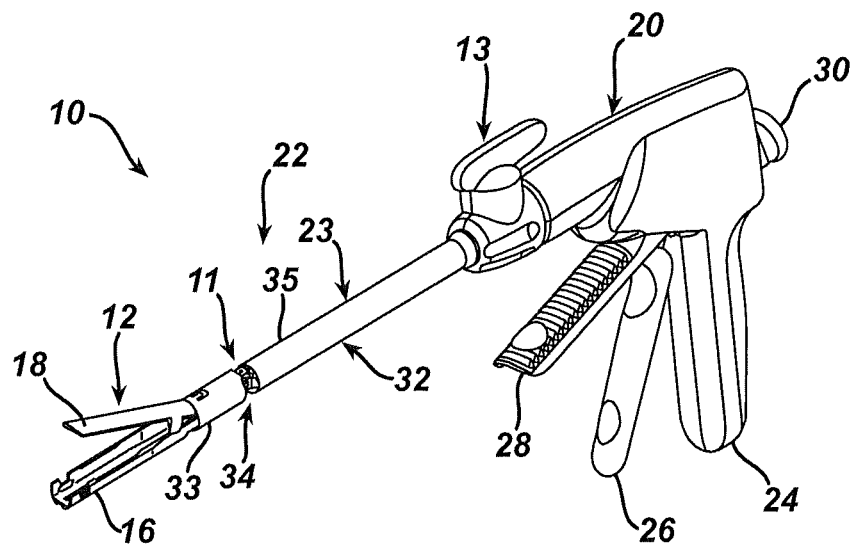
FIG. 1A depicts a perspective view of an articulating surgical instrument with an end effector in a nonarticulated position.
Figure 1B:
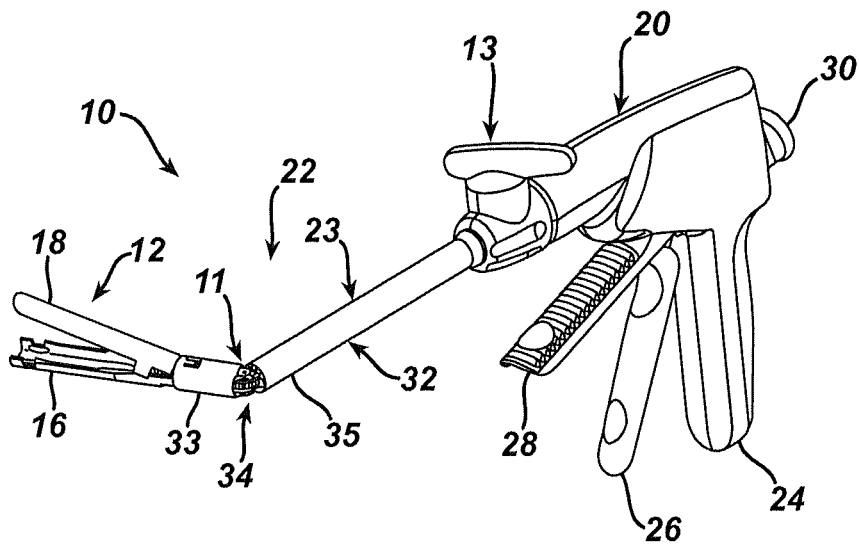
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
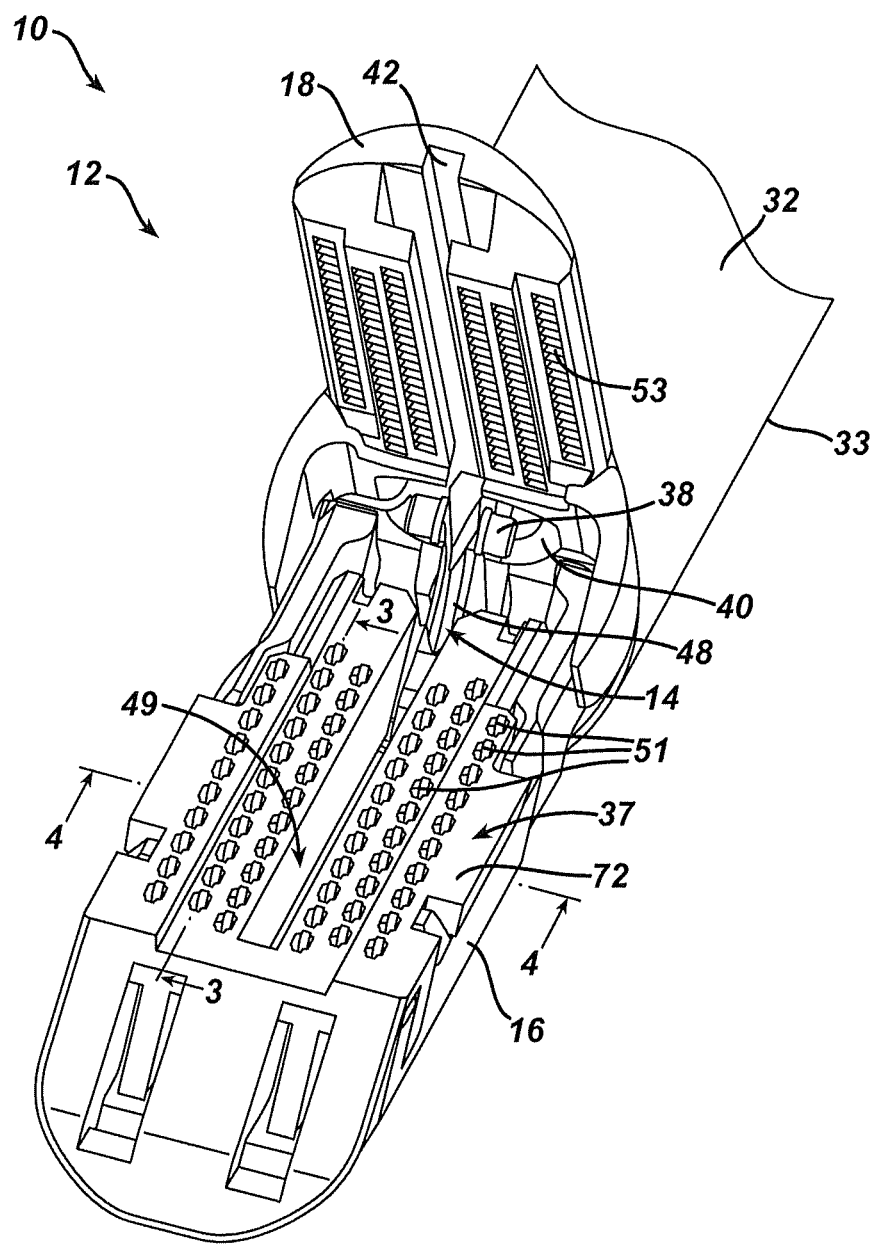
FIG. 2 depicts a perspective view of an opened end effector of the surgical instrument of FIGS. 1A-1B.
Figure 3A:
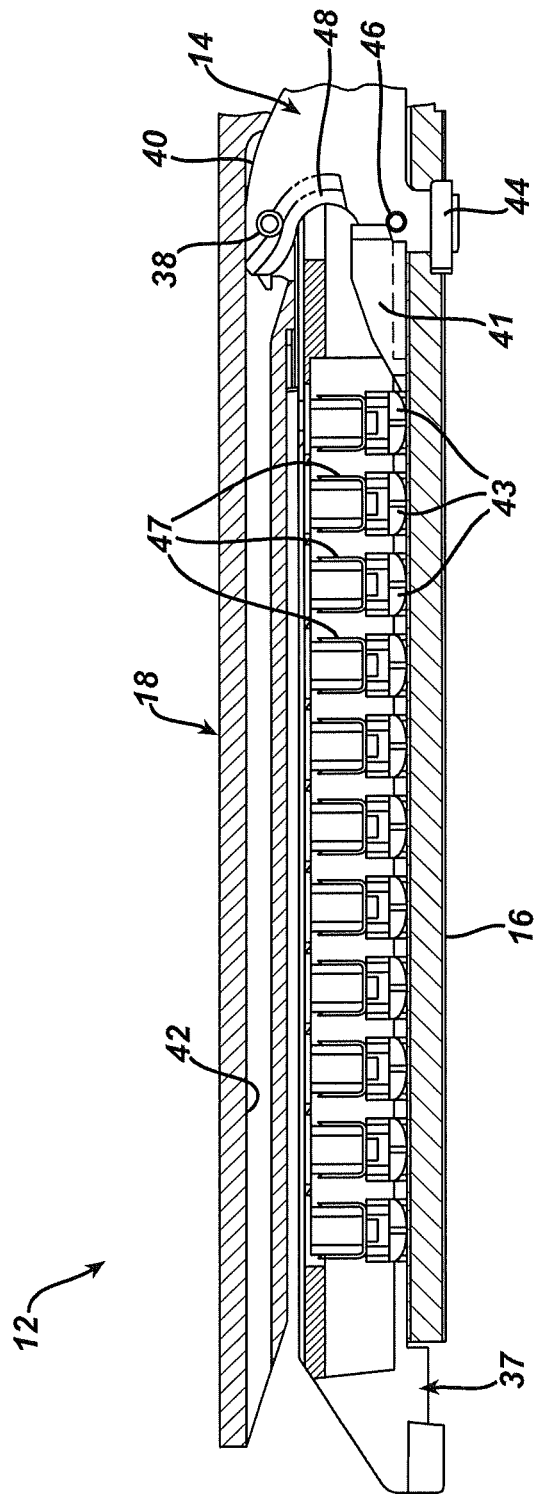
FIG. 3A depicts a side cross-sectional view of the end effector of FIG. 2, taken along line 3-3 of FIG. 2, with the firing bar in a proximal position.
Figure 3B:
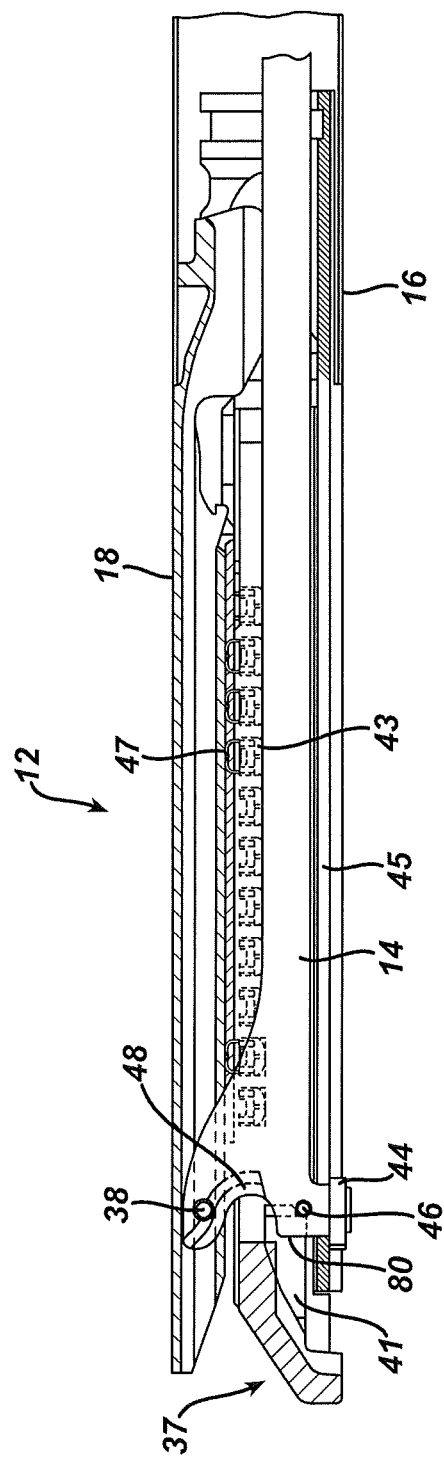
FIG. 3B depicts a side cross-sectional view of the end effector of FIG. 2, taken along line 3-3 of FIG. 2, but showing the firing bar in a distal position.
Figure 4:
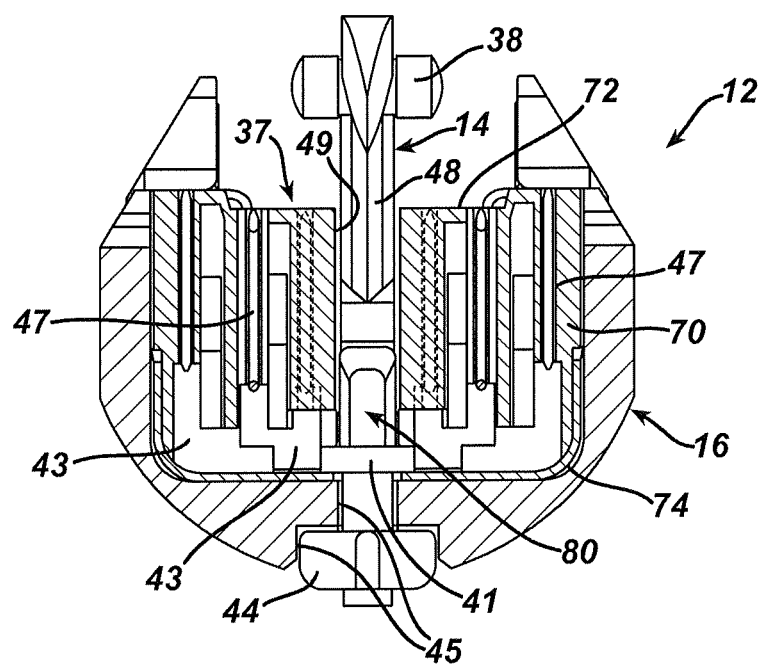
FIG. 4 depicts an end cross-sectional view of the end effector of FIG. 2, taken along line 4-4 of FIG. 2.
Figure 5:
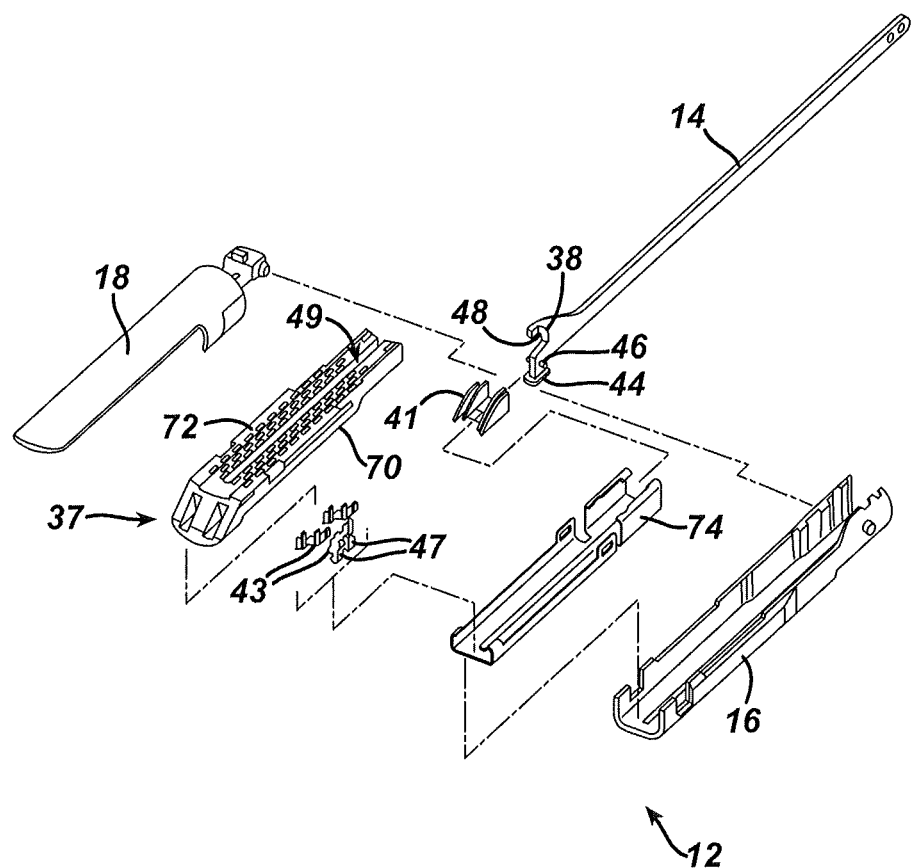
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (70) on one side of vertical slot (49), with another set of three rows of staple apertures (51) being formed through upper deck (70) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
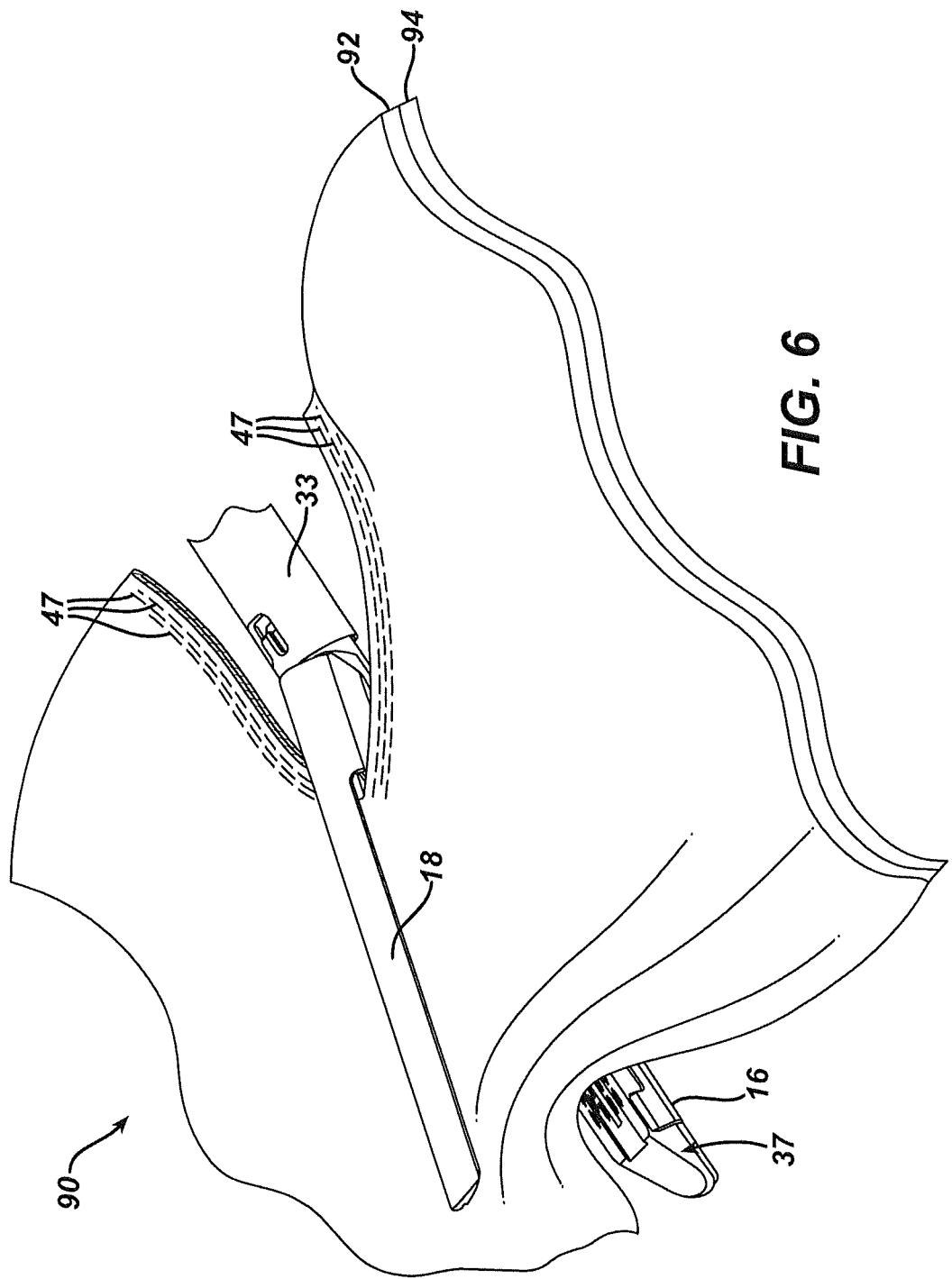
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,964,363; U.S. Pat. No. 6,978,921; U.S. Pat. No. 6,988,649; U.S. Pat. No. 7,000,818; U.S. Pat. No. 7,111,769; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; and/or U.S. Pat. No. 7,455,208. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Modular End Effector

Figure 7:
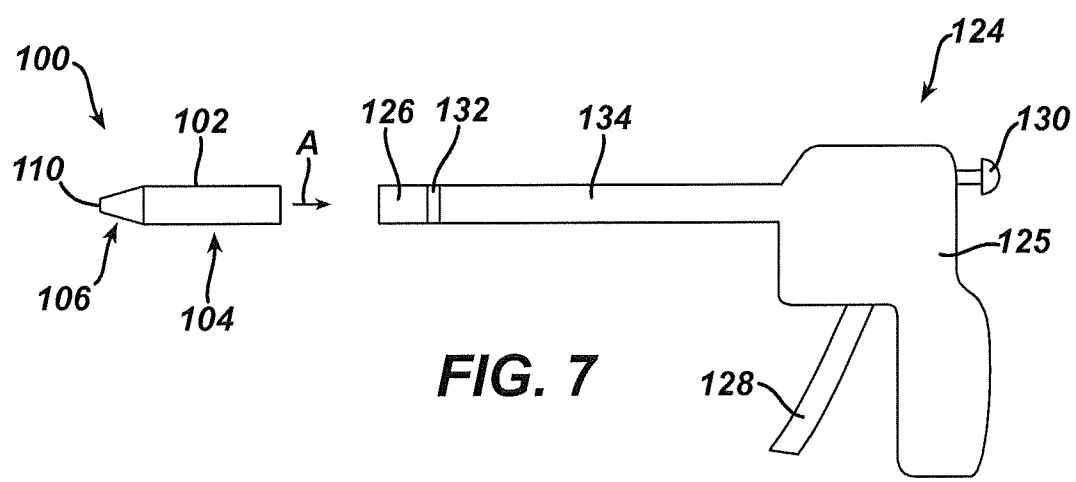
FIG. 7 depicts an exemplary therapeutic agent end effector and an associated dedicated device.
Figure 8:
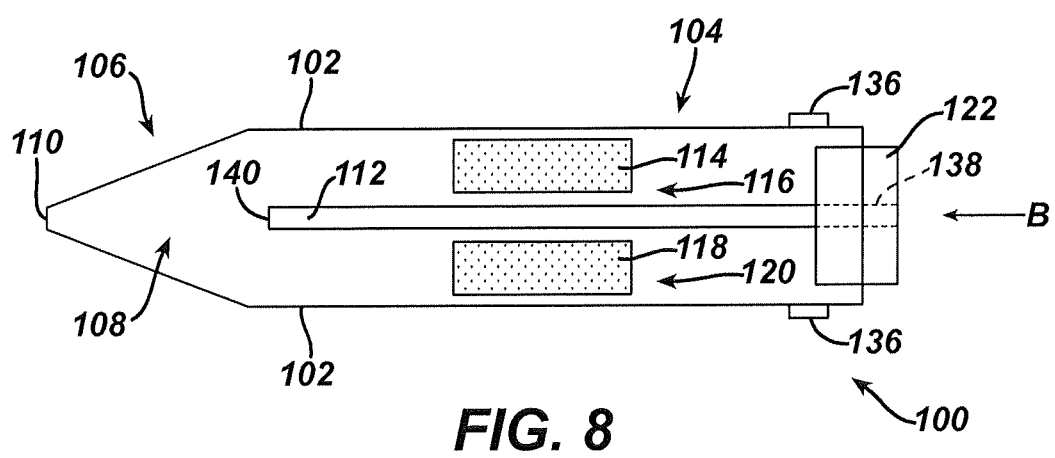
FIG. 8 depicts a side cross-sectional view of the end effector of FIG. 7.

FIGS. 7-8 show an exemplary modular end effector (100) for delivery of a therapeutic agent onto tissue after use of a stapling device, such as instrument (10). As shown in FIG. 8, end effector (100) includes exterior walls (102) defining proximal portion (104) and distal portion (106), distal portion (106) including mixing space (108) and tip (110). By way of example only, tip (110) and exterior walls (102) may be constructed and operable in accordance with the teachings of U.S. Patent App. Pub. No. 2008/0121657, entitled "Adhesive Dispenser for Surgery", published May 29, 2008, now U.S. Pat. No. 7,861,893, issued Jan. 4, 2011, the disclosure of which is incorporated by reference herein.

End effector (100) also includes reservoirs or capsules of separate reagents on separate sides of interior wall (112) along proximal portion (104) of end effector (100) to prevent premature mixing of the reagents. For example, first agent (114) is disposed in first holding space (116) on one side of wall (112) and second agent (118) is disposed in second holding space (120) on the other side of wall (112). As will be described below, application of distally directed force against piston (122) will allow for the reagents to mix at distal portion (106) of end effector (100) and be applied to tissue at a desirable location via expulsion through an orifice formed at tip (110).

Such reagents may include but are not limited to medical fluid components such as thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

In some versions, a medical fluid may be suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly (oxyalkylene), copolymers of poly(ethylene oxide)-poly (propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

Modular end effector (100) may be used as a replaceable and removably attachable end effector (100) with a device such as instrument (10) or may be used with a dedicated device, such as device (124) shown in FIG. 7. End effector (100) may be sized for receipt through conventional trocars of various inner diameters. Referring back to FIG. 7, end effector (100) is positioned at a distal end of shaft (134), which is configured to removably receive end effector (100) via ring (126). End effector (100) is inserted into ring (126) in the direction of arrow (A) shown in FIG. 7. End effector (100) is removably attached to ring (126) at the distal end of device (124), with extended ends or protrusions (136) for example, which may be received into corresponding notches (not shown) of ring (126). Conversely, ring (126) may include protrusions received into corresponding notches of end effector (100) to attach ring (126) to end effector (100). Of course, ring (126) and end effector (100) may include a variety of other components or features that are operable to removably secure end effector (100) to shaft (134) of device (124).

Device (124) of the present example includes trigger (128) to apply force against piston (122) disposed at a proximal end of end effector (100), as shown in FIG. 8, to move piston (122) in a distal direction. Additionally, a knob (130) is disposed at a proximal, upper portion of device (124) on handpiece (125). Knob (130) is connected to articulation segment (132) at the distal end of shaft (134) such that articulation or actuation of knob (130) provides a corresponding articulation of articulation segment (132), allowing ring (126) and attached end effector (100) to be moved to a desired position above staples (47). Articulation segment (132) may articulate in a horizontal plane along which a longitudinal axis of shaft (134) of device (124) is positioned and/or a vertical plane transverse to the horizontal plane. A horizontal or vertical articulation of knob (130) (e.g., by a user's thumb) effects a corresponding, respective horizontal or vertical articulation of articulation segment (132). Alternatively, a clockwise or counter-clockwise rotation of knob (130) may effect a corresponding articulation in a selected plane (either the horizontal or vertical plane, for example). End effector (100) and/or shaft (134) of device (124) may also be rotatable relative to the handpiece (125) about a longitudinal axis defined by shaft (124).

Application of force to trigger (128) results in an application of force in the direction of arrow (B) of FIG. 8 to apply force to piston (122) of end effector (100). Various suitable components and configurations that may be used to convert actuation of trigger (128) into actuation of piston (122) will be apparent to those of ordinary skill in the art in view of the teachings herein. While handpiece (125) is formed as a pistol grip with pivoting trigger (128), it should be understood that handpiece (125) and trigger (128) may have any other suitable configuration.

Figure 10:
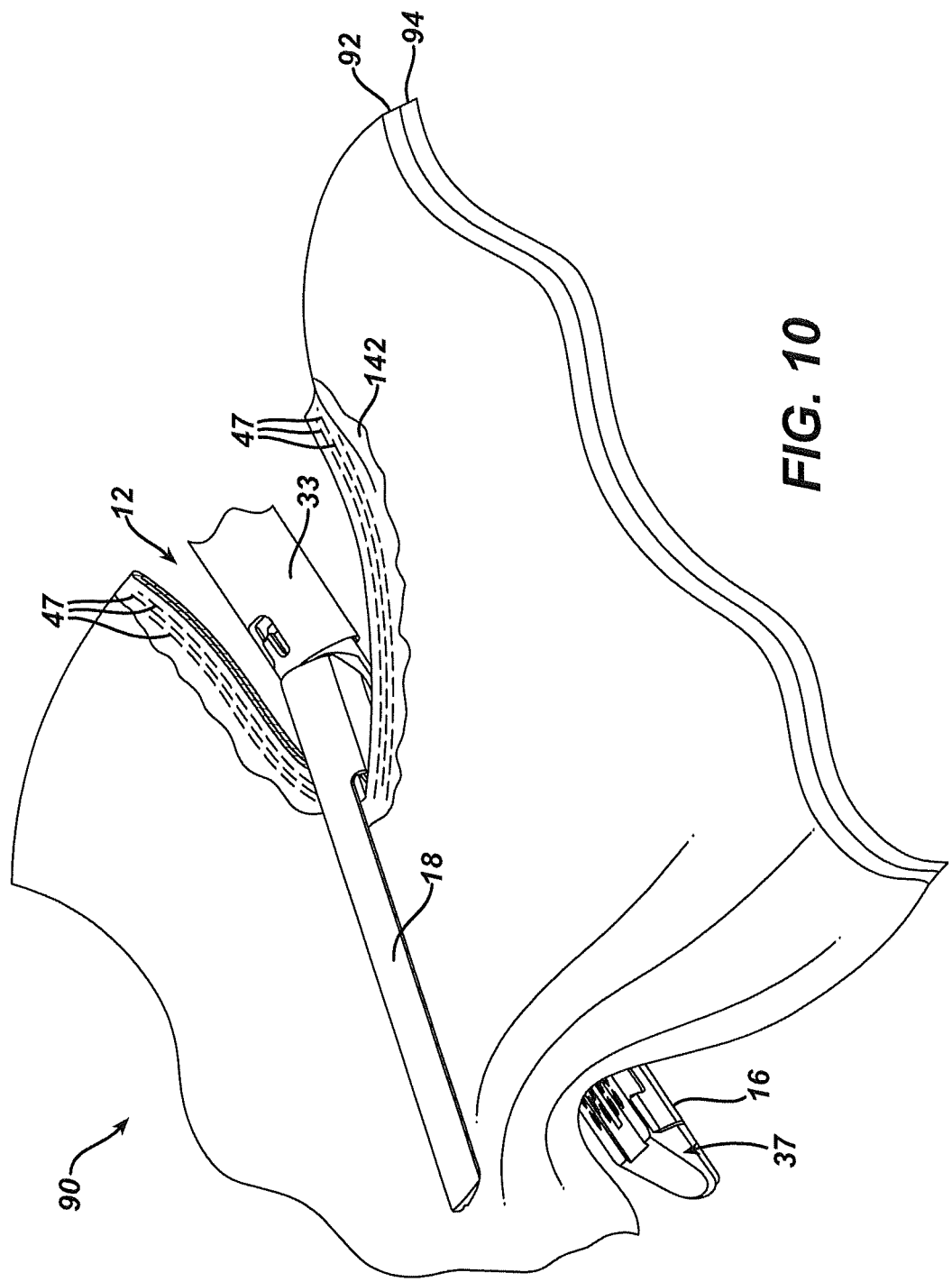
FIG. 10 depicts a perspective view of an end effector with the cartridge assembly of FIG. 9, the end effector positioned at and actuated within the tissue.

Piston (122) may comprise a single plunger with aperture (138) to receive wall (112) of end effector (100) or may include a dual plunger formation with each side movable down a side of wall (112). Piston (122) moves distally along wall (112) to apply force against proximal ends of reservoirs or agents (114, 118) on either side of wall (112) to move agents (114, 118) distally towards tip (110). Distal portion (106) of end effector (100) includes tip (110), which has an aperture through which a spray or other liquid form may be dispelled, for example. Tip (110) also includes mixing space (108) defined by end (140) of wall (112) and exterior walls (102) of end effector (100). Agents (114, 118), one of which may be fibrin and the other of which may be thrombin, for example, are moved towards and past end (140) of wall (112) to mix together in mixing space (108) before being expelled through the aperture of tip (110) onto staples (47) of tissue (90), for example, as shown in FIG. 10, as therapeutic agent or tissue repair composition (142).

Use of end effector (100) either with an instrument such as instrument (10) described further above or dedicated device (124) may prevent waste of reagents during delivery, which may occur where reservoirs of material are located near a handle portion of the associated instrument or device. In such locations, reagents may travel further along a lumen within the shaft of the respective instrument or device and have portions remain in the lumen as waste during such travel. Along with a reduced amount of waste, use of end effector (100) may allow for a reduced amount of reagent to be used within the reservoirs or capsules than would otherwise be used if the reagent was positioned near a handle portion of an instrument or device used to expel such reagent onto tissue.

III. Exemplary Foam Block Integral with End Effector Cartridge

Figure 9:
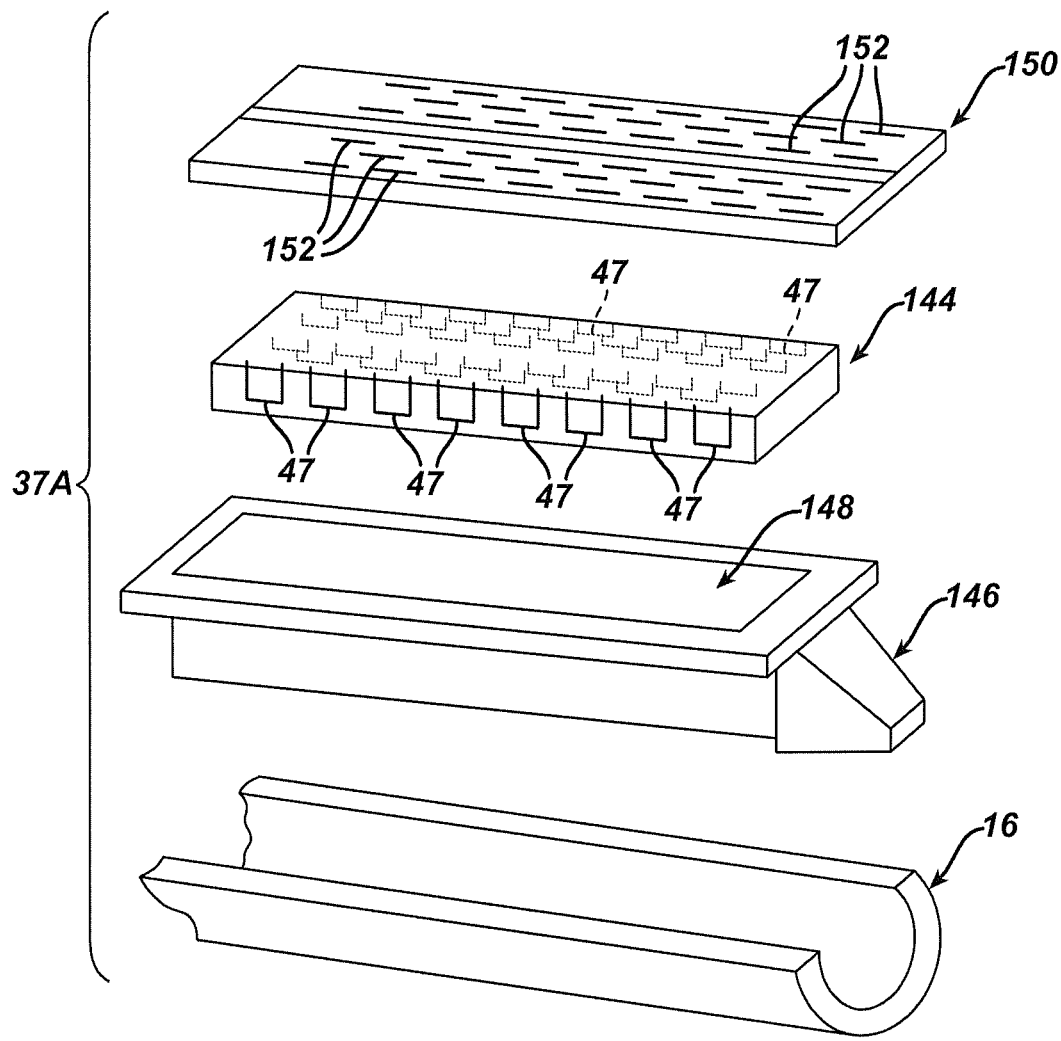
FIG. 9 depicts an exploded perspective view of an exemplary alternative cartridge assembly for an end effector.

In another version shown in FIG. 9, cartridge (37A) as described above may include an integral foam block (144) containing an agent, such as a hemostatic agent, to assist with the reduction of bleeding associated with the severing and stapling of tissue via end effector (12), as described above. FIG. 9 shows an exploded view of cartridge (37A) for removable installation into a channel of lower jaw (16) of instrument (10), which operates to sever and/or staple tissue as described above. Cartridge bottom (146) includes chamber (148) defined by peripheral walls of cartridge bottom (146) into which foam block (144) is inserted. Staples (47) may be pre-installed into foam block (144). Alternatively, block (144) may be positioned between staples (47) and the underside of a cartridge deck, such as lid (150). Staples (47) may comprise a material selected from iron, nickel titanium alloy, stainless steel, and/or titanium. Of course, any other suitable material(s) may be used to form staples (47).

The material for foam block (144) may comprise, for example, adjunct or hemostatic agents such as fibrin or thrombin or those described above that assist to coagulate blood and reduce the amount of bleeding at the surgical site. The hemostatic abilities of such adjuncts may also contribute to the use of such adjuncts as adhesives and sealants. The agents may assist to coagulate blood at a surgical site which allows tissue surrounding such blood to stick together and may prevent leaks along the stapled tissue site, for example.

While a foam block is described in the example herein, the material may alternatively comprise a fibrous pad, a matrix, a mesh, or another structure, in accordance with the teachings of, by way of example, U.S. Patent App. Pub. No. 2009/0120994, entitled "Surgical Fastening Device with Initiator Impregnation of a Matrix or Buttress to Improve Adhesive Application", published May 14, 2009, now U.S. Pat. No. 7,708,180, issued May 4, 2010, the disclosure of which is incorporated by reference herein. The material may comprise, for example, a biocompatible material that is a buttress, a matrix having a plurality of openings therein, an open cell foam, a closed cell foam, and/or a fabric pad. The material may have a plurality of openings and may be a foam material containing such openings, or a mesh, or a threadlike structure, and may include porosities that induce a wicking feature to drawing adhesive into the material and ensure the openings remain clear of the adhesive, allowing tissue growth through the openings after application to tissue.

Cartridge (37A) may have a greater height with an integral foam block (144) than without such a foam block, allowing for staples of longer leg length to be used. Lid (150) includes apertures (152) through which staples (47) may be driven and an elongated slot through which firing bar (14) may be fired, as described above. Lid (150) is disposed over foam block (144) and may be snap fit to cartridge bottom (146) of cartridge (37A), for example. Alternatively, lid (150) may be molded to cartridge bottom (146) of cartridge (37A). Other suitable relationships between lid (150) and cartridge bottom (146) will be apparent to those of ordinary skill in the art in view of the teachings herein.

As shown in FIG. 10, when end effector (12) including cartridge (37A) is used, reagent is applied to tissue (90) during the driving of staples (47) into tissue (90) as staples (47) are advanced through foam block (144) for receipt against anvil (18) and form into closed staples (47) capturing tissue (90). Cartridge (37A) and/or anvil (18) may additionally include a separate layer of adjunct or agent that may activate upon receiving the foam of the coated staples to allow the adjunct to spread onto tissue (90) along with receipt of the staples (47) onto tissue (90). For example, one of thrombin or fibrin may be included and freeze dried with saline in foam block (144) and may activate upon being mixed with the other of thrombin or fibrin when staples (47) from within foam block (144) are driven up towards anvil (18), which may be coated with the other reagent.

As staples (47) are driven up towards anvil (18), staples (47) may be kept substantially vertically oriented by initial placement in such a direction when embedded in foam block (144). Alternatively, if staples (47) are disposed below foam block (144) in chamber (148) of cartridge bottom (146), staples (47) may be kept substantially vertically oriented as staples (47) are driven up towards anvil (18) in a similar manner as described above for staples (47) in cartridge (37). Chamber (148) of cartridge bottom (146) may include internal vertical walls, similar to those shown in FIG. 4, defining vertical slots configured to receive staples (47) and keep staples (47) substantially vertically oriented prior to and during the driving of staples (47) up towards anvil (18). In particular, each staple (47) is driven vertically within the body of cartridge (37A) by a staple driver (43) to drive staple (47) out through an associated staple aperture (152). Wedge sled (41) presents inclined cam surfaces that urge staple drivers (43) upwardly as wedge sled (41) is driven distally through staple cartridge (37A).

To accommodate the presence of foam block (144) in cartridge (37A), wedge sled (41) and/or staple drivers (43) may be modified to be increased in size or in the strength of material used to form wedge sled (41) and/or staple drivers (43). The modifications may be made to provide an additional force sufficient to drive staples (47) through foam block (144) and out through staple apertures (152) of lid (150) and into forming contact with staple forming pockets (53) on anvil (18). The increases in size and/or material strength properties would be comparative to the respective amounts used for wedge sled (41) and/or staple drivers (43) to drive staples (47) in cartridge (37) out through staple apertures (51) and into forming contact with staple forming pockets (53) on anvil (18), as described above.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising a body, a shaft housing a firing bar, an end effector comprising an anvil, a lower jaw, and a stapling and severing mechanism responsive to a longitudinal closing motion produced by the body and the shaft, the lower jaw configured to receive a cartridge when in an open position, the cartridge comprising:

(a) a cartridge bottom including walls defining a chamber;
(b) a plurality of staples disposed in the chamber;
(c) a foam block disposed in the chamber, wherein the foam block comprises a therapeutic material; and (d) a lid disposed over the foam block and the chamber, wherein the lid comprises a plurality of apertures configured for receipt of the plurality of staples upon activation of the stapling and severing mechanism in response to the longitudinal closing motion, wherein the staples are configured to be driven through the foam block and coated with the therapeutic material in response to activation of the stapling and severing mechanism, wherein the plurality of staples are embedded in the foam block.

2. The cartridge of claim 1, wherein the lid comprises a slot configured for receipt of the firing bar upon activation of the stapling and severing mechanism in response to the longitudinal closing motion.

3. The cartridge of claim 1, wherein the plurality of staples are disposed below the foam block.

4. The cartridge of claim 1, wherein the lid is snap-fit to the cartridge bottom.

5. The cartridge of claim 1, wherein the lid is molded to the cartridge bottom.

6. The cartridge of claim 1, wherein one of the plurality of staples comprises a material selected from at least one of the following materials: iron, nickel titanium alloy, stainless steel, and titanium.

7. The cartridge of claim 1, wherein the plurality of staples are disposed in vertical slots defined by internals walls within the chamber.

8. The cartridge of claim 1, wherein a staple driver is substantially aligned with a respective one of the plurality of staples and is configured to drive the staple through the foam block upon activation of the stapling and severing mechanism in response to the longitudinal closing motion.

9. The cartridge of claim 8, wherein the instrument comprises a wedge sled configured to drive the staple driver toward the anvil upon activation of the stapling and severing mechanism in response to the longitudinal closing motion.

10. The cartridge of claim 1, wherein the foam block comprises thrombin.

11. The cartridge of claim 1, wherein the foam block comprises fibrin.

12. The cartridge of claim 1, wherein the foam block comprises one of thrombin or fibrin, and the anvil is coated with the other of thrombin or fibrin.

13. The cartridge of claim 1, wherein one of thrombin or fibrin is freeze dried with saline in the foam block.

14. A surgical instrument comprising:
(a) a body;
(b) a shaft housing a firing bar;
(c) an end effector comprising:
  (i) an anvil, wherein the anvil is coated with a first coagulating agent,
  (ii) an upper jaw,
  (iii) a lower jaw, and
  (iv) a stapling and severing mechanism responsive to a longitudinal closing motion produced by the body and the firing bar, wherein the upper and lower jaws are configured to move relative to one another to clamp tissue; and
(d) a cartridge configured to be received by the lower jaw when the upper jaw is in an open position, wherein the cartridge comprises:
  (i) a cartridge bottom including walls defining a chamber,
  (ii) a plurality of staples disposed in the chamber,
  (iii) a foam block disposed in the chamber, wherein the foam block comprises a second coagulating agent, and
  (iv) a lid disposed over the foam block and the chamber, wherein the staples are configured to be driven out of the foam block and out of the lid and toward the anvil in response to the longitudinal closing motion produced by the body and the firing bar, wherein the staples are configured to be coated with the second coagulating agent as the staples are driven out of the foam block, wherein the first coagulating agent is configured to react with the second coagulating agent when the staples contact the anvil.

15. A surgical instrument, comprising:
(a) a body;
(b) a shaft housing a firing bar;
(c) an end effector comprising;
  (i) an anvil,
  (ii) a lower jaw, and
  (iii) a stapling and severing assembly responsive to a longitudinal closing motion produced by the body and the firing bar; and
(d) a removable cartridge, wherein the lower jaw is configured to receive the cartridge when the end effector is in an open configuration, the cartridge comprising:
  (i) a housing having a plurality of sidewalls and a bottom portion,
  (ii) a plurality of staples disposed in the housing,
  (iii) a foam block disposed in the housing, and
  (iii) a deck disposed over the plurality of staples and the foam block, the deck defining apertures, each aperture being substantially disposed over a corresponding staple of the plurality of staples,
wherein a portion of foam block is configured to coat the staples in response to the longitudinal closing motion produced by the body and the firing bar, wherein a portion of the foam block is configured to remain within the housing under the deck after the staples are driven from the cartridge in response to the longitudinal closing motion produced by the body and the firing bar.

* * * * *